(12) United States Patent
Konno et al.

(10) Patent No.: US 10,345,257 B2
(45) Date of Patent: Jul. 9, 2019

(54) GAS SENSOR

(71) Applicant: NGK Spark Plug Co., LTD., Nagoya (JP)

(72) Inventors: Takashi Konno, Komaki (JP); Tomohiro Wakazono, Konan (JP); Kentaro Kamada, Komaki (JP); Hitoshi Furuta, Tajimi (JP); Masaki Nakagawa, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 74 days.

(21) Appl. No.: 15/715,781

(22) Filed: Sep. 26, 2017

(65) Prior Publication Data

US 2018/0095051 A1    Apr. 5, 2018

(30) Foreign Application Priority Data

Sep. 30, 2016  (JP) .................................. 2016-193372

(51) Int. Cl.
| | |
|---|---|
| *G01N 27/406* | (2006.01) |
| *G01N 27/407* | (2006.01) |
| *G01N 27/28* | (2006.01) |
| *G01N 27/409* | (2006.01) |
| *C03C 8/02* | (2006.01) |
| *G01N 27/41* | (2006.01) |
| *C03C 3/087* | (2006.01) |

(52) U.S. Cl.
CPC ......... *G01N 27/4077* (2013.01); *C03C 3/087* (2013.01); *C03C 8/02* (2013.01); *G01N 27/409* (2013.01); *G01N 27/4067* (2013.01); *G01N 27/41* (2013.01)

(58) Field of Classification Search
CPC ...... G01N 27/28; G01N 27/304; G01N 27/30; G01N 27/403; G01N 27/406; G01N 27/407; G01N 27/409; G01N 27/41
See application file for complete search history.

(56) References Cited

U.S. PATENT DOCUMENTS

| | | |
|---|---|---|
| 2006/0185978 A1 | 8/2006 | Nagao et al. |
| 2011/0220496 A1 | 9/2011 | Oya et al. |

FOREIGN PATENT DOCUMENTS

| | | |
|---|---|---|
| JP | 2006-250925 A | 9/2006 |
| JP | 5638984 B | 10/2014 |

*Primary Examiner* — Susan D Leong
(74) *Attorney, Agent, or Firm* — Leason Ellis LLP

(57) ABSTRACT

The gas sensor includes a gas sensor element, a casing, and an insulating inner member contained inside the casing. The gas sensor element includes a detection element and a heater. The detection element includes one or more cells each having a solid electrolyte body and a pair of electrodes. Each of the opposite side surfaces of the detection element includes a region including a smallest current cell and extending forward of the smallest current cell in the direction of an axial line. The region and the forward-facing surface of the detection element are covered with a glass coating having a glass transition point of higher than 700° C. but not higher than 800° C. and a porosity of 3.0% or less. The detection element is controlled to have a temperature equal to or lower than the glass transition point of the glass coating.

4 Claims, 4 Drawing Sheets

GAS SENSOR

This application claims the benefit of Japanese Patent Application No. 2016-193372, filed Sep. 30, 2016, which is incorporated herein by reference in its entirety.

FIELD OF THE INVENTION

The present invention relates to a gas sensor that detects the concentration of a specific gas such as oxygen or NOx contained in combustion gas or exhaust gas from a combustor, an internal combustion engine, etc.

BACKGROUND OF THE INVENTION

In one conventional gas sensor attached to an exhaust system such as an exhaust pipe of an engine to detect the concentration of a specific gas component in the exhaust gas, a heater and a detection element including at least one cell in which a pair of electrodes are disposed on surfaces of a solid electrolyte body are stacked and integrated together.

In the gas sensor configured as described above, the solid electrolyte body is exposed at side surfaces of the detection element, and electrically conductive materials such as soot contained in the exhaust gas can adhere to the exposed portion of the solid electrolyte body. The solid electrolyte body has a portion which is heated to a temperature which is lower than the temperature at which the soot burns out (about 600° C.) and at which the solid electrolyte body exhibits oxygen ion conductivity (e.g., 200 to 600° C.). If soot adheres to such a portion, the soot causes a leakage current, and the gas concentration detection performance of the gas sensor deteriorates.

One technique developed to address this issue is to apply a paste composed mainly of alumina to the exposed portion of the solid electrolyte body, which is heated to a temperature lower than 600° C. during the use of the gas sensor element, to thereby insulate the exposed portion (see, for example, Japanese Patent Application Laid-Open (kokai) No. 2006-250925).

When the alumina paste is applied to the solid electrolyte body by printing, pinholes are formed. One technique developed to address this issue is to insulate the exposed portion of the solid electrolyte body using, instead of alumina, a glass coating having a glass transition point higher than 700° C. (see, for example, Japanese Patent No. 5638984 (FIG. 2)).

Problems to be Solved by the Invention

A forward end portion of the detection element is heated to high temperature by the exhaust gas etc., and the soot adhering to the forward end portion burns out. Therefore, in the technique described in Patent Document 2, side surfaces of the forward end portion of the detection element are not covered with the glass coating. The forward end portion of the detection element includes a section heated to a temperature exceeding the glass transition point of the glass coating (i.e., 700° C. or higher). Also from this point of view, the forward end portion of the detection element that is heated to a temperature higher than 700° C. is not covered with the glass coating.

It has been found that, when non-burnable electrically conductive materials such as Na in the exhaust gas adhere to a solid electrolyte layer exposed at the forward end portion of the detection element, the characteristics of the sensor may vary. Unlike soot, inorganic materials such as Na do not burn out at a high temperature equal to or higher than 600° C. and remain adhering to the high-temperature forward end portion of the detection element. In particular, when Na etc. adhere to the solid electrolyte layer of a cell in which the current flowing between the pair of electrodes becomes the smallest when the gas sensor element is controlled, current leakage occurs, and the current between the electrodes fluctuates largely.

Accordingly, it is an object of the present invention to provide a gas sensor in which a forward end part of an exposed portion of a solid electrolyte body, which part is heated to high temperature, is covered with a glass coating having a high glass transition point so as to prevent changes in the characteristics of the gas sensor, which changes would otherwise occur due to adhesion of non-burnable electrically conductive materials such as Na to the solid electrolyte body.

SUMMARY OF THE INVENTION

Means for Solving the Problems

In order to solve the above-described problem, the present invention provides a gas sensor which comprise a gas sensor element extending in the direction of an axial line and having a forward end portion to be exposed to a gas to be measured (target gas); a metallic casing that surrounds a circumference of the gas sensor element and has a forward end from which the forward end portion of the gas sensor element protrudes; and an insulating inner member contained inside the casing and surrounding the circumference of the gas sensor element. The gas sensor element includes a detection element including one or more cells each having a solid electrolyte body and a pair of electrodes, the one or more cells including a smallest current cell in which the smallest current among the cells flows between the pair of electrodes when the gas sensor element is controlled; and a heater stacked on the detection element and including a heat generating element disposed at least in a location that corresponds to the smallest current cell in the direction of the axial line. The solid electrolyte body of the smallest current cell has end faces extending along opposite side surfaces of the detection element and further has an end face extending along a forward-facing surface of the detection element. Each of the opposite side surfaces of the detection element has a region including the smallest current cell and extending forward of the smallest current cell in the direction of the axial line, and the region of each of the opposite side surfaces of the detection element and the forward-facing surface of the detection element are covered with a glass coating having a glass transition point of higher than 700° C. but not higher than 800° C. and a porosity of 3.0% or less. The detection element is controlled at a temperature equal to or lower than the glass transition point of the glass coating.

As described above, in the present invention, at least the smallest current cell in which the smallest current among the cells flows between the pair of electrodes when the gas sensor element is controlled, is insulated and covered with the glass coating. This can prevent the occurrence of a leakage current caused by adhesion of non-burnable electrically conductive materials such as Na contained in the target gas to the solid electrolyte layer of the smallest current cell, so that changes in the characteristics of the gas sensor caused by a large change in the current between the electrodes of the smallest current cell can be prevented. The leakage current means that the detection element and the metallic casing are electrically connected through the electrically conductive materials such as Na.

Unlike soot, inorganic materials such as Na do not burn out even at a high temperature of 600° C. or higher. In view of this, the glass coating is formed so as to insulate and cover all surface portions (i.e., the opposite side surfaces and forward-facing surface of the detection element) of the detection element, which portions are heated to a temperature higher than the temperature of regions of the opposite side surfaces corresponding to the smallest current cell.

The glass transition point of the glass coating is higher than 700° C. In this case, even when the solid electrolyte body is heated to 600° C. or higher which is a temperature range in which electrically conductive materials such as soot contained in the target gas can be burnt out, cracking of the glass coating caused by increased thermal expansion due to transition of the glass coating to a supercooled liquid can be prevented, and collapse of the glass coating caused by melting of the glass due to reaction with impurities (such as alkali metal elements, Pb, P, and Zn) can be prevented.

The higher the glass transition point of the glass coating, the more desirable in terms of heat resistance, but the more the denseness of the coating tends to decrease. When the denseness of the coating decreases, electrically conductive materials such as Na in the target gas pass through pinholes of the coating and adhere to the end faces of the solid electrolyte layer, and this may cause changes in the characteristics of the sensor. To achieve the heat resistance and denseness of the coating simultaneously, the glass transition point is set to 800° C. or lower.

Moisture etc. with the electrically conductive materials such as Na in the target gas dissolved therein may adhere to the glass coating. To prevent such moisture etc. from reaching the solid electrolyte layer through the pinholes in the coating, the porosity of the glass coating is set to 3.0% or less.

In the gas sensor of the present invention, the glass coating may cover portions of the opposite side surfaces of the detection element, the portions extending from the region to a forward end of the inner member in the direction of the axial line.

In this gas sensor, the glass coating can also serve as an insulating coating for a portion of the detection element, which portion is heated to a temperature lower than the temperature of the smallest current cell, i.e., is heated to the temperature at which the solid electrolyte body exhibits oxygen ion conductivity (e.g., 200 to 600° C.) and which is lower than the temperature at which soot burns out (about 600° C.). The occurrence of a leakage current due to soot can thereby be prevented, and deterioration in gas concentration detection performance can be prevented.

In the gas sensor of the present invention, the detection element may further include a space into which the target gas is introduced; a first oxygen pump cell which includes a first solid electrolyte body and a pair of first pump electrodes disposed on the first solid electrolyte body, one of the first pump electrodes being exposed to the space, the first oxygen pump cell pumping oxygen from/into the target gas in the space; an oxygen concentration detection cell which includes a second solid electrolyte body, a detection electrode disposed on the second solid electrolyte body and exposed to the interior of the space, and a reference electrode serving as a counter electrode for the detection electrode, an electromotive force being generated between the reference electrode and the detection electrode; a measurement chamber into which the target gas in the space is introduced; and a second oxygen pump cell which is the smallest current cell and which includes a third solid electrolyte body, an inner second pump electrode disposed on the third solid electrolyte body and exposed to the measurement chamber, and a counter second pump electrode serving as a counter electrode for the inner second pump electrode, the second oxygen pump cell detecting the concentration of NOx in the target gas in the measurement chamber, wherein the space is formed between the first solid electrolyte body and the second solid electrolyte body stacked that the first solid electrolyte body and the second solid electrolyte body are spaced apart from each other, and the gas sensor element serves as an NOx sensor element.

This gas sensor includes the three cells. The glass coating is formed on the side surfaces of the detection element having the second oxygen pump cell serving as the smallest current cell. This can prevent the current flowing between the pair of second pump electrodes from being affected by the leakage current.

Effects of the Invention

In the present invention, the forward end part, which is to be heated to high temperature, of the exposed portion of the solid electrolyte body is covered with the glass coating having a high glass transition point. Therefore, it is possible to prevent changes in the characteristics of the gas sensor, which changes would otherwise occur due to adhesion of non-burnable electrically conductive materials such as Na to the solid electrolyte body.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An embodiment of the present invention will next be described.

Figure 1:
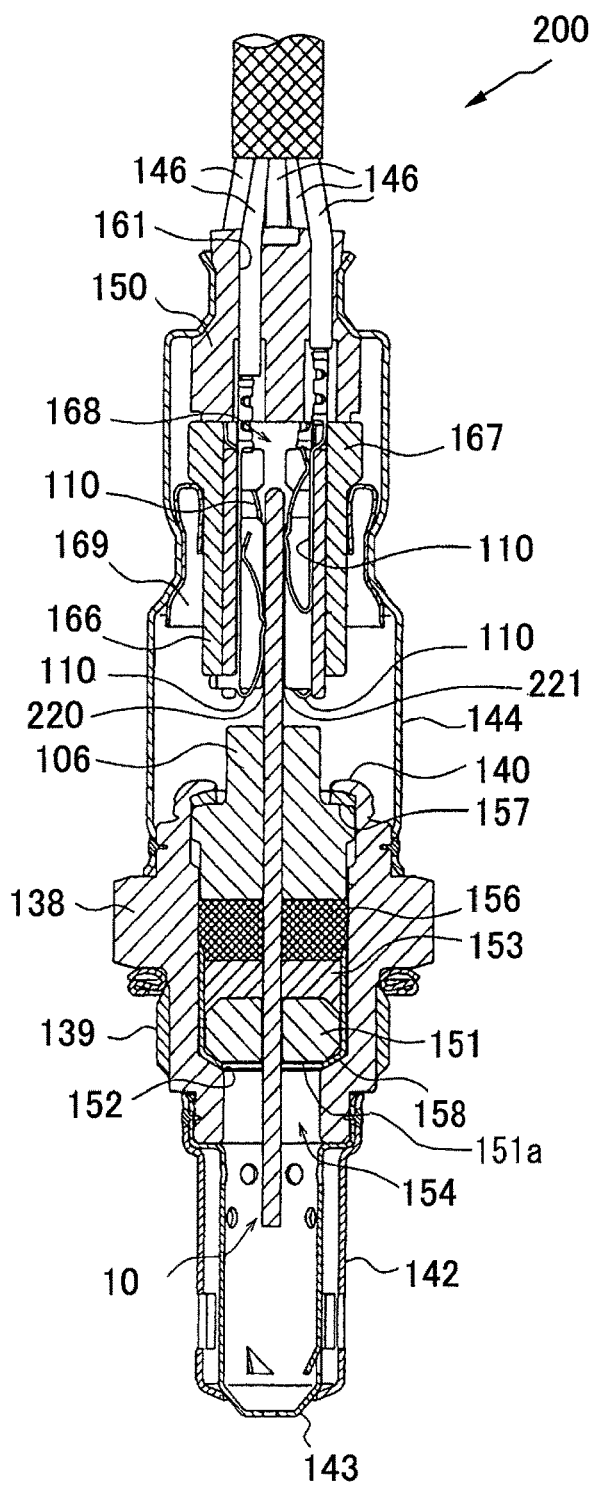
FIG. 1 is a cross-sectional view of an NOx sensor according to an embodiment of the present invention, the cross-sectional view being taken in the direction of an axial line of the NOx sensor.
Figure 2:
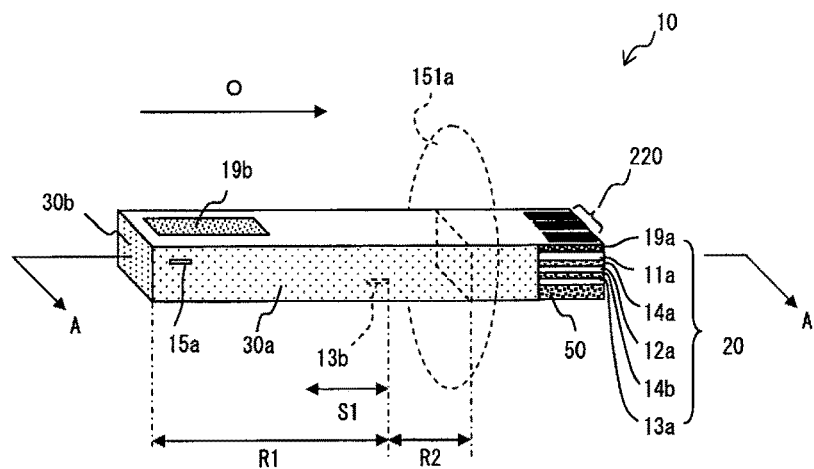
FIG. 2 is a perspective view of an NOx sensor element.
Figure 3:
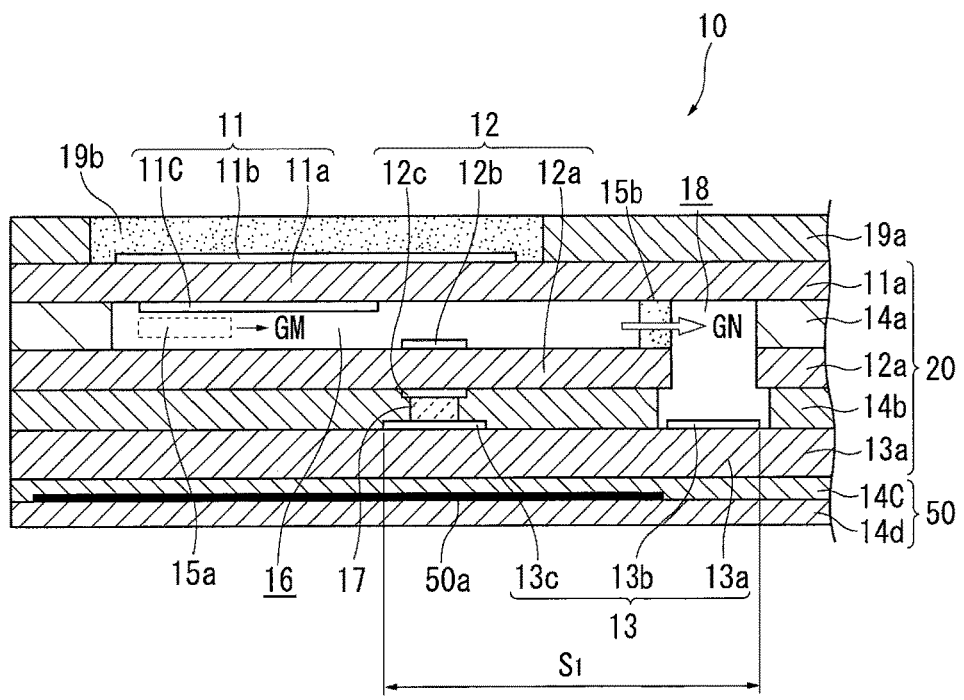
FIG. 3 is a cross-sectional view of the NOx sensor element taken along line A-A in FIG. 2 (a cross-sectional view in the direction of stacking of layers) and showing a forward end portion of the NOx sensor element.

FIG. 1 is a general cross-sectional view of a gas sensor (NOx sensor) 200 according to the embodiment of the present invention, the cross-sectional view being taken in the direction of an axial line of the NOx sensor 200. FIG. 2 is a perspective view of an NOx sensor element 10, and FIG. 3 is a cross-sectional view of the NOx sensor element 10 taken along line A-A in FIG. 2 (in the direction of the axial line) and showing a forward end portion of the NOx sensor element 10.

As shown in FIG. 1, the NOx sensor 200 includes: a tubular metallic shell (corresponding to the "casing" in the claims) 138 having a threaded portion 139 formed on the outer surface of the metallic shell 138 to fix it to an exhaust pipe; the plate-shaped NOx sensor element (corresponding to the "gas sensor element" in the claims) 10 extending in the direction of the axial line (the direction of the axial line of the NOx sensor 200: the vertical direction in the figure); a tubular ceramic sleeve 106 disposed so as to surround the circumference of the NOx sensor element 10; an insulating contact member 166 that has a contact insertion hole 168 extending therethrough in the axial direction and is disposed such that the inner wall surface of the contact insertion hole 168 surrounds a rear end portion of the NOx sensor element 10; and six connection terminals 110 (only two are shown in FIG. 1) disposed between the NOx sensor element 10 and the insulating contact member 166.

The metallic shell 138 is made of stainless steel and has a generally tubular shape. The metallic shell 138 has a through hole 154 extending in the axial direction and a ledge 152 protruding radially inward within the through hole 154. The NOx sensor element 10 is disposed in the through hole 154 such that a forward end portion of the NOx sensor element 10 protrudes from the forward end of the through hole 154. The ledge 152 has an inward tapered surface inclined with respect to a plane perpendicular to the axial direction.

An alumina-made annular ceramic holder 151, powder charged layers 153 and 156 (hereinafter may be referred to as talc rings 153 and 156), and the above-described ceramic sleeve 106 are stacked in this order from the forward end side toward the rear end side within the through hole 154 of the metallic shell 138 so as to surround the circumference of the NOx sensor element 10. The insulating ceramic holder 151 located forwardmost and surrounding the circumference of the NOx sensor element 10 corresponds to the "inner member" in the claims. The forward end of the ceramic holder 151 is denoted by a numeral 151a.

A crimp packing 157 is disposed between the ceramic sleeve 106 and a rear end portion 140 of the metallic shell 138, and a metallic holder 158 for holding the talc ring 153 and the ceramic holder 151 is disposed between the ceramic holder 151 and the ledge 152 of the metallic shell 138. The rear end portion 140 of the metallic shell 138 is crimped such that the ceramic sleeve 106 is pressed toward the forward end side through the crimp packing 157. With this configuration, even when the NOx sensor element 10 is exposed to a gas to be measured such as exhaust gas, almost no electrically conductive materials such as soot adhere to a portion of the surface of the NOx sensor element 10 which portion is located rearward of the forward end 151a of the ceramic holder 151.

As shown in FIG. 1, a double protector made of a metal (e.g., stainless steel), having a plurality of holes, and including an external protector 142 and an internal protector 143 is attached to a forward (lower in FIG. 1) outer circumference of the metallic shell 138 by, for example, welding so as to cover the protruding portion of the NOx sensor element 10.

An outer tube 144 is fixed to a rear outer circumference of the metallic shell 138. A grommet 150 is disposed in a rear (upper in FIG. 1) opening of the outer tube 144. The grommet 150 has six lead wire insertion holes 161 into which six lead wires 146 (only five lead wires are shown in FIG. 1) are inserted, and the lead wires 146 are electrically connected to six electrode terminals 220 and 221 (only two electrode terminals are shown in FIG. 1) of the NOx sensor element 10.

The insulating contact member 166 is disposed on the rear side (the upper side in FIG. 1) of the NOx sensor element 10 protruding from the rear end portion 140 of the metallic shell 138. The insulating contact member 166 is disposed around the electrode terminals 220 and 221 formed on opposite surfaces of a rear end portion of the NOx sensor element 10. The insulating contact member 166 is formed into a tubular shape with the contact insertion hole 168 extending therethrough in the axial direction and has a flange portion 167 protruding radially outward from the outer surface of the insulating contact member 166. The flange portion 167 abuts against the outer tube 144 through a holding member 169, whereby the insulating contact member 166 is held inside the outer tube 144.

As shown in FIG. 2, the NOx sensor element 10 has a structure including an insulating layer 19a, a first solid electrolyte layer 11a, an insulating layer 14a, a second solid electrolyte layer 12a, an insulating layer 14b, a third solid electrolyte layer 13a, and insulating layers 14c and 14d that are stacked in this order. These layers 19a, 11a, 14a, 12a, 14b, and 13a and unillustrated electrodes form a detection element 20.

A heater 50 is stacked on the lower surface of the detection element 20, and the heater 50 and the detection element 20 form the NOx sensor element 10. The heater 50 includes insulating layers 14c and 14d and an unillustrated heat generating element. The detailed structure of the NOx sensor element 10 will be described later.

The first solid electrolyte layer 11a, the second solid electrolyte layer 12a, and the third solid electrolyte layer 13a correspond to the "solid electrolyte bodies" in the claims.

The solid electrolyte bodies used in the present embodiment are formed from a partially stabilized zirconia sintered body including a mixture of C, M, and T phases (cubic, monoclinic, and tetragonal crystals). In this case, part of the M and T phases in the solid electrolyte body undergo monoclinic (M phase)/tetragonal (T phase) transformation accompanied by a volume change at 700 to 1,100° C. at which the M/T transformation occurs. As a result of the behavior of the thermal expansion coefficient of the solid electrolyte bodies at that time, a glass coating which will be described later always receives compressive force even when a volume change due to heating or cooling of the detection element occurs. This is because the thermal expansion coefficient of the glass coating is always smaller than the thermal expansion coefficient of the solid electrolyte bodies in a temperature range equal to or lower than the glass transition point. One feature of glass and ceramics such as alumina is that they can well withstand compressive stress but cannot withstand tensile stress. Therefore, even when a volume change occurs, cracking is unlikely to occur in the glass coating, and its durability is high.

Even when the glass coating is temporarily heated to a temperature equal to or higher than the glass transition point, cracking is unlikely to occur in the glass coating, because in this temperature range, the viscosity of the glass decreases, and the glass coating becomes flowable. Therefore, the glass coating is high in durability.

In FIG. 2, end faces of each of the first solid electrolyte layer 11a, the second solid electrolyte layer 12a, and the third solid electrolyte layer 13a extend along the forward-facing surface of the detection element 20 and its opposite side surfaces (surfaces extending in the stacking direction of the first solid electrolyte layer 11a and the second solid electrolyte layer 12a, in the direction of the axial line O, and in the direction of the thickness of each solid electrolyte layer).

Specifically, before the glass coating described later is formed, the first solid electrolyte layer 11a, the second solid electrolyte layer 12a, and the third solid electrolyte layer 13a are exposed at the opposite side surfaces and forward-facing surface of the detection element 20.

The present invention does not encompass a detection element structure of the type in which a solid electrolyte body is fitted in a through hole formed in an insulating layer such that the end faces of the solid electrolyte body are covered with the insulating layer.

Each of the opposite side surfaces of the detection element 20 has a region R1 covered with a glass coating 30a. The region R1 includes an inner second pump electrode 13b (a smallest current cell 13 described later) and extends forward of the inner second pump electrode 13b in the direction of the axial line O. The forward-facing surface of the detection element 20 is also covered with a glass coating 30b.

In the present embodiment, the glass coating 30a is disposed also in a region R2 extending rearward from the region R1 to at least the forward end 151a of the ceramic holder 151. More specifically, the glass coating 30a extends rearward of the forward end 151a. The forward end 151a of the ceramic holder 151 is located rearward of the inner second pump electrode 13b.

An opening for introducing a gas to be measured into the detection element 20 is provided on each of the opposite side surfaces of the detection element 20, and a first diffusion resistor 15a is disposed in the opening. The details of this will be described later. Since the glass coatings 30a and 30b are not gas permeable, the glass coating 30a is formed so as not to cover the first diffusion resistor 15a, as shown in FIG. 2, in order not to prevent the introduction of the gas to be measured.

The detection element 20 and the heater 50 are stacked and integrated together. Therefore, the regions R1 of the opposite side surfaces of the NOx sensor element 10 and its forward-facing surface may be coated with the glass coatings 30a and 30b with no distinction made between the detection element 20 and the heater 50. In the present embodiment, as shown in FIG. 2, the glass coatings 30a and 30b are formed on the regions R1 and R2 of the opposite side surfaces and the forward-facing surface of the entire NOx sensor element 10; i.e., the regions R1 and R2 of the opposite side surfaces and the forward-facing surface of the detection element 20 and the regions R1 and R2 of the opposite side surfaces and the forward-facing surface of the heater 50. The "stacking direction" is a direction passing through the layers 19a to 13a of the detection element 20 and is the vertical direction in FIG. 2.

The glass coatings 30a and 30b are formed of glass having a glass transition point of higher than 700° C. but not higher than 800° C. and a porosity of 3.0% or less. This glass may be amorphous glass having a composition containing at least $SiO_2$: 40 to 70 wt %, $Al_2O_3$: 10 to 30 wt %, and alkaline-earth oxide (at least one selected from the group consisting of MgO, CaO, SrO, and BaO): 10 to 45 wt % in total. The alkaline-earth oxide contained in the composition of the glass prevents a reduction in insulating properties of the glass coatings 30a and 30b and improves the meltability of a glass slurry.

If the glass transition point of the glass coatings 30a and 30b is 700° C. or lower, the following problem occurs. As will be described later, when the control temperature of a detection electrode 12b reaches 600 to 700° C., the temperature of the solid electrolyte layers reach a temperature near 700° C. In this case, the glass coatings 30a and 30b undergo transition to a supercooled liquid, and cracking may occur in the glass coatings, or the glass coatings may react with impurities and may be fused and collapsed. In this case, the glass coatings become unstable, and their heat resistance deteriorates.

The higher the glass transition point of the glass coatings 30a and 30b, the more desirable in terms of heat resistance, but the more the denseness of the coatings tends to decrease. When the denseness of the coatings decreases, electrically conductive materials such as Na in the gas to be measured pass through pinholes of the coatings and adhere to the end faces of the solid electrolyte layers 11a, 12a, and 13a, and this may cause changes in the characteristics of the sensor. Therefore, the glass transition point is set to 800° C. or lower in order to allow the coatings to have heat resistance and denseness simultaneously.

To prevent the electrically conductive materials such as Na in the gas to be measured from adhering to the solid electrolyte layers through the pinholes of the coatings, the porosity of the glass coatings 30a and 30b is set to 3.0% or less.

The porosity is computed using a pore diameter distribution measured by a mercury intrusion method according to JIS-R1655.

The glass coatings 30a and 30b can be formed by applying a slurry prepared by dispersing a mixture of a glass raw material powder and other components (such as a sintering control agent) to the side surfaces and forward-facing surface of the NOx sensor element 10 and then firing the slurry at a prescribed temperature (e.g., 900 to 1,400° C.). The leveling properties of the slurry (glass slurry) containing the glass component after its application are good, and pinholes are unlikely to be formed. Therefore, a film with no open pores can be obtained by one application, and the productivity of the film when the glass slurry is applied is higher than when an alumina paste is applied. The firing temperature of the glass slurry is lower than the firing temperature of the NOx sensor element 10. Therefore, after the NOx sensor element 10 is produced by firing, the glass slurry is applied and fired.

No particular limitation is imposed on the thickness of the glass coatings 30a and 30b, and the thickness may be about 1/10 to about 1/500 of the thickness of the NOx sensor element 10 in the stacking direction.

As described above, the regions R1 of the opposite side surfaces of the NOx sensor element 10 (the detection element 20) and its forward-facing surface are covered with the glass coatings 30a and 30b. As a result, at least the smallest current cell 13 which is the smallest among the cells in terms of the current flowing between the pair of electrodes when the gas sensor element is controlled (a region S1 including the inner second pump electrode 13b and described later) is coated and insulated. This can prevent the occurrence of a leakage current caused by adhesion of non-burnable electrically conductive materials such as Na contained in the gas to be measured to the third solid electrolyte layer 13a of the smallest current cell 13, so that changes in the characteristics of the gas sensor caused by a large change in the current between the electrodes of the smallest current cell 13 can be prevented.

Unlike soot, inorganic materials such as Na do not burn out even at a high temperature of 600° C. or higher. The side surfaces of the detection element 20 include portions that are heated to a temperature higher than the temperature of regions of the opposite side surfaces which regions correspond to the smallest current cell 13 (the inner second pump electrode 13b). It is necessary that all these portions (i.e., the regions R1 and forward-facing surface of the detection element 20) be coated and insulated.

Meanwhile, it is unnecessary to cover, with the glass coating 30a, portions of the opposite side surfaces of the NOx sensor element 10 (the detection element 20), the portions extending rearward of the region R1. However, it is preferable to cover the region R2 with the glass coating 30a. With this configuration, the glass coating 30a can also serve as an insulating coating for a portion that is heated to the temperature at which the solid electrolyte bodies exhibit oxygen ion conductivity (e.g., 200 to 600° C.) and which is lower than the temperature at which soot burns out (about 600° C.). The occurrence of a leakage current due to soot can thereby be prevented, and deterioration in gas concentration detection performance can be prevented.

More preferably, a region extending rearward from the region R2 to the rear end of the ceramic holder 151 is also covered with the glass coating 30a, as in the present embodiment. With this configuration, even if soot enters the gap between the ceramic holder 151 and the NOx sensor element 10, the soot does not adhere to the NOx sensor element 10.

The glass coating 30a formed in a region rearward of the region R1 may have the same composition as the glass coatings 30a and 30b formed in the region R1 and on the forward-facing surface of the detection element or may have a different composition. In both cases, it is preferable that the glass coating 30a contains Li, Na, K, Rb, Cs, Pb each in an amount of 3,000 mass ppm or less or does not contain these elements. If the content of any one of these elements exceeds 3,000 mass ppm, the insulating properties and heat resistance of the glass coatings 30a and 30b may deteriorate. More preferably, the glass coatings 30a and 30b do not contain Li, Na, K, Rb, Cs, and Pb (0 ppm), but these elements may be contained as unavoidable impurities.

When the composition of the glass coating 30a formed in the region rearward of the region R1 differs from the compositions of the glass coatings 30a and 30b formed in the region R1 and on the forward-facing surface of the detection element, it is preferable that the glass coating 30a formed in the portion rearward of the region R1 contains 1 to 50% by mass of $Al_2O_3$. When the content of $Al_2O_3$ is 1% by mass or more, the insulating properties at high temperature are improved, and the heat resistance is improved by the anchoring effect of the $Al_2O_3$ particles. However, if the content of $Al_2O_3$ exceeds 50% by mass, the flowability of the glass becomes low, and the leveling properties during sintering deteriorate, so that pinholes may be formed.

It is preferable in terms of heat resistance and environmental measures that the glass coatings 30a and 30b disposed rearward and forward of the region R1 contain no Pb.

The material forming the glass coatings 30a and 30b is not limited to amorphous glass. For example, when the glass slurry contains 2 to 35% by mass of a nucleating agent (at least one selected from the group consisting of $TiO_2$, $ZrO_2$, $Fe_2O_3$, $V_2O_5$, NiO, $Cr_2O_3$, Pt, and Au), the glass in the slurry is crystallized by firing, and crystallized glass is formed. This is preferable because the heat resistance is improved. The crystallized glass refers to a glass whose glass transition point (an endothermic reaction) can be measured by DTA (differential thermal analysis) before firing and which crystallizes as a result of firing (e.g., at 900° C.) and after that does not cause an endothermic reaction in the DTA (differential thermal analysis) at least in a temperature range (±100° C.) close to the transition point before firing.

Examples of the composition of the glass containing the nucleating agent include glass compositions containing silica powder, alkaline-earth oxide, $TiO_2$ (the nucleating agent), rare-earth oxide, ZnO, and $B_2O_3$. Examples of the rare-earth oxide include $La_2O_3$, $Y_2O_3$, $CeO_2$, $Pr_6O_{11}$, and $Nd_2O_3$. The rare-earth oxide is preferably $La_2O_3$.

Referring next to FIG. 3, a cross-sectional structure of the forward end portion of the NOx sensor element 10 will be described.

The NOx sensor element 10 has a structure including the insulating layer 19a, the first solid electrolyte layer 11a, the insulating layer 14a, the second solid electrolyte layer 12a, the insulating layer 14b, the third solid electrolyte layer 13a, and the insulating layers 14c and 14d that are stacked in this order. The first solid electrolyte layer 11a and the second solid electrolyte layer 12a are stacked through the insulating layer 14a so as to be spaced apart from each other, and a detection chamber 16 is formed between these solid electrolyte layers. The gas to be measured GM is introduced from the outside into the detection chamber 16 through the first diffusion resistors 15a disposed in the openings on the opposite side surfaces of the detection chamber 16.

A second diffusion resistor 15b is disposed at the rear end of the detection chamber 16, and a measurement chamber 18 in communication with the detection chamber 16 through the second diffusion resistor 15b is formed rearward (on the right side in FIG. 3) of the detection chamber 16. The measurement chamber 18 passes through the second solid electrolyte layer 12a and is formed between the first solid electrolyte layer 11a and the third solid electrolyte layer 13a.

The detection chamber 16 corresponds to the "space" in the claims.

A long plate-shaped heat generating element 50a extending in the direction of the axial line of the NOx sensor element 10 is embedded between the insulating layers 14c and 14d. The heat generating element 50a is used to heat the detection element 20 to its activation temperature. The oxygen ion conductivity of the solid electrolyte layers 11a to 13a is thereby increased, and the operation of the NOx sensor element 10 is stabilized. The heat generating element 50a is sandwiched between the insulating layers 14c and 14d, and the heat generating element 50a and the insulating layers 14c and 14d form the heater 50 having the heat generating element 50a.

The insulating layers 14a to 14d and 19a are composed mainly of alumina, and the first diffusion resistors 15a, the second diffusion resistor 15b, and a porous layer 19b described later are formed of a porous material such as alumina. The heat generating element 50a is formed from, for example, platinum.

A first oxygen pump cell 11 includes the first solid electrolyte layer 11a composed mainly of zirconia having oxygen ion conductivity and further includes an inner first pump electrode 11c and a first counter electrode (outer first pump electrode) 11b that are disposed so as to sandwich the first solid electrolyte layer 11a therebetween, and the inner first pump electrode 11c is exposed to the detection chamber 16. The inner first pump electrode 11c and the outer first pump electrode 11b are composed mainly of platinum. The inner first pump electrode 11c and the outer first pump electrode 11b correspond to the "pair of first pump electrodes" in the claims.

The insulating layer 19a is stacked on a surface of the first solid electrolyte layer 11a and on a surface of the first counter electrode 11b. A portion of the insulating layer 19a that covers the first counter electrode 11b is cut away to form a cutout space, and the porous layer 19b is disposed in the cutout space. Since the porous layer 19b is gas permeable, oxygen pumping is not affected even when the electrode 11b is covered with the porous layer 19b.

An oxygen concentration detection cell 12 includes the second solid electrolyte layer 12a composed mainly of zirconia and further includes the detection electrode 12b and a reference electrode 12c that are disposed so as to sandwich the second solid electrolyte layer 12a therebetween, and the detection electrode 12b is exposed to the detection chamber 16 at a position downstream of the inner first pump electrode 11c. The detection electrode 12b and the reference electrode 12c are composed mainly of platinum.

The insulating layer 14b is cut such that the reference electrode 12c in contact with the second solid electrolyte layer 12a is disposed in a cutout space formed as a result of the cutting, and the cutout space is filled with a porous body to form a reference oxygen chamber 17. A weak constant current is applied to the oxygen concentration detection cell 12 in advance to pump oxygen from the detection chamber 16 into the reference oxygen chamber 17, so that a reference oxygen atmosphere is formed around the reference electrode 12c.

A second oxygen pump cell 13 includes the third solid electrolyte layer 13a composed mainly of zirconia, the inner second pump electrode 13b disposed on a surface of the third solid electrolyte layer 13a that is exposed to the measurement chamber 18, and a second counter electrode (a counter second pump electrode 13c). The inner second pump electrode 13b and the counter second pump electrode 13c are composed mainly of platinum.

The counter second pump electrode 13c is disposed on the third solid electrolyte layer 13a to be located in a cutout space of the insulating layer 14b and exposed to the reference oxygen chamber 17 so as to face the reference electrode 12c. The inner second pump electrode 13b is disposed rearward of the counter second pump electrode 13c.

The first oxygen pump cell 11, the oxygen concentration detection cell 12, and the second oxygen pump cell 13 correspond to the "cells" in the claims. The current flowing between the electrodes 13b and 13c of the second oxygen pump cell 13 is the smallest among the currents flowing between the electrodes of the above-described cells, and therefore the second oxygen pump cell 13 corresponds to the "smallest current cell" in the claims.

The region of the "smallest current cell" that extends in the direction of the axial line O is the entire axial region including the electrodes 13b and 13c and a portion of the third solid electrolyte layer 13a that extends between the electrodes 13b and 13c. Specifically, in the example in FIG. 3, the region S1 extending from the forward end of the counter second pump electrode 13c to the rear end of the inner second pump electrode 13b and including the third solid electrolyte layer 13a is referred to as the second oxygen pump cell 13 (smallest current cell).

The heat generating element 50a of the heater 50 is disposed at least in a location that corresponds to the second oxygen pump cell 13 (smallest current cell) in the direction of the axial line O. The phrase "location that corresponds to" means that the heat generating element 50a at least partially overlaps the second oxygen pump cell 13 (region S1) in the direction of the axial line O of the NOx sensor element 10. Specifically, when the heat generating element 50a at least partially overlaps the second oxygen pump cell 13, the temperature of the second oxygen pump cell 13 can be well controlled by the heater 50. The rest of the heat generating element 50a may be located rearward of the rear end of the second oxygen pump cell 13 or located forward of the forward end of the second oxygen pump cell 13. Preferably, the control temperature of the second oxygen pump cell 13 is, for example, 600 to 700° C. so that the operation of the solid electrolyte layers 11a to 13a can be stabilized.

The region R1 including the smallest current cell in the direction of the axial line O is a region including the entire region S1 forming the smallest current cell (the second oxygen pump cell 13). For example, in the case of FIGS. 2 and 3, the region R1 includes the rear end of the inner second pump electrode 13b and extends to the forward end of the NOx sensor element 10 (the detection element 20).

An example of the operation of the NOx sensor element 10 will next be described. When an engine is started and electric power is supplied from an external power source, the heat generating element 50a is energized through a known control circuit (not shown) to heat the first oxygen pump cell 11, the oxygen concentration detection cell 12, and the second oxygen pump cell 13 to their activation temperatures. The gas to be measured (exhaust gas) GM flowing into the detection chamber 16 contains excess oxygen. When the cells 11 to 13 are heated to the activation temperatures, the first oxygen pump cell 11 pumps the excess oxygen in the gas to be measured GM from the inner first pump electrode 11c to the first counter electrode 11b.

At that time, oxygen in the detection chamber 16 has a concentration corresponding to the electromotive force (interelectrode voltage) Vs generated between the electrodes of the oxygen concentration detection cell 12. Therefore, by controlling the magnitude and direction of a first pump current Ip1 applied to the first oxygen pump cell 11 such that the interelectrode voltage Vs becomes a constant voltage V1 (e.g., 425 mV), the concentration of oxygen in the detection chamber 16 can be adjusted to a prescribed low oxygen concentration.

The gas to be measured GN with the oxygen concentration adjusted flows toward the measurement chamber 18. By applying, to the second oxygen pump cell 13, a constant voltage Vp2 (e.g., 450 mV) at which NOx in the gas to be measured GN is decomposed into oxygen and $N_2$, NOx is decomposed into nitrogen and oxygen. Then a second pump current Ip2 flows through the second oxygen pump cell 13 such that the oxygen generated as a result of the decomposition of NOx is pumped from the measurement chamber 18. An approximately linear relation exists between the second pump current Ip2 and the concentration of NOx. Therefore, by detecting the second pump current Ip2, the concentration of NOx in the gas to be measured can be detected.

It will be appreciated that the present invention is not limited to the embodiment described above and encompasses various modifications and equivalents within the spirit and scope of the present invention.

For example, in the above embodiment, the opposite side surfaces of the detection element 20 and its forward-facing surface are covered with the glass coating. The front and rear surfaces (two surfaces adjacent to the side surfaces) of the detection element 20 may also be covered with the glass coating.

A porous insulating ceramic film may be formed so as to externally cover the glass coating. This can prevent peeling of the glass coating, which would otherwise start from its forward end portion, and the durability of the glass coating is improved.

In the above embodiment, the detection electrode 12b is disposed in the detection chamber 16 to which the inner first pump electrode 11c is exposed, as shown in FIG. 3. Instead, the detection electrode 12*b* may be disposed in a chamber other than the detection chamber 16. Such an NOx sensor element structure is described in, for example, Japanese Patent Application Laid-Open (kokai) No. 2004-354400 (FIG. 3). This NOx sensor element includes two solid electrolyte layers. Specifically, in this NOx sensor element structure, a single layer serves as both the second solid electrolyte body 12*a* and the third solid electrolyte body 13*a*.

Similarly, an NOx sensor element structure in which a single layer serves as both the first solid electrolyte body 11*a* and the third solid electrolyte body 13*a* may be used.

Examples of the gas sensor include, in addition to the NOx sensor, an oxygen sensor.

In the above embodiment, on each of the opposite surfaces of the detection element 20, the entire side surface of the region R1 forward of the inner second pump electrode 13*b* is covered with the glass coating 30*a* as shown in FIG. 2.

Figure 4:
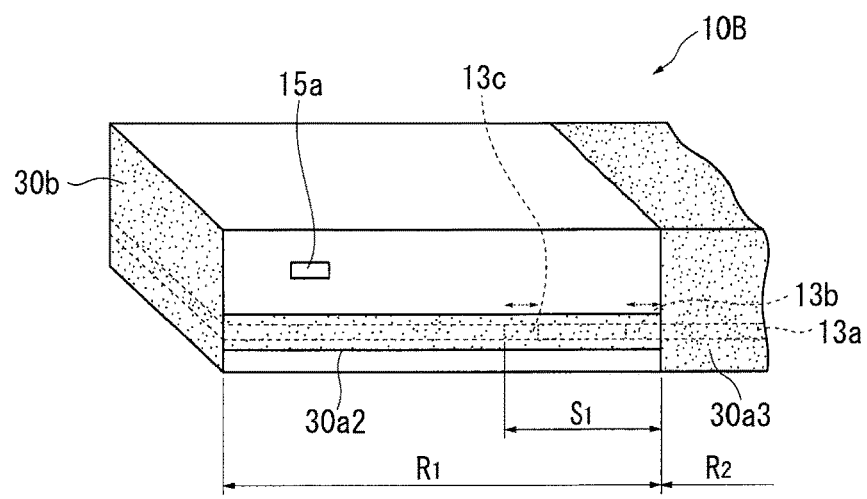
FIG. 4 is a perspective view showing a modification of glass coatings that cover the NOx sensor element.

However, as shown in an NOx sensor element 10B in FIG. 4, a glass coating 30*a*2 may be formed to cover only a stripe-shaped portion of the region R1, which portion is located at the same position as the smallest current cell 13 in the stacking direction (the vertical direction in FIG. 4) of the detection element 20 and covers the smallest current cell 13 only. In the NOx sensor element 10B, the entire circumferential surface in the region R2 is covered with a glass coating 30*a*3. The glass coating 30*a*3 can be formed by stamp-printing the paste for the glass coating, and the glass coating 30*a*2 can be formed by applying the paste for the glass coating into a stripe shape using a dispenser (an injector).

Figure 5:
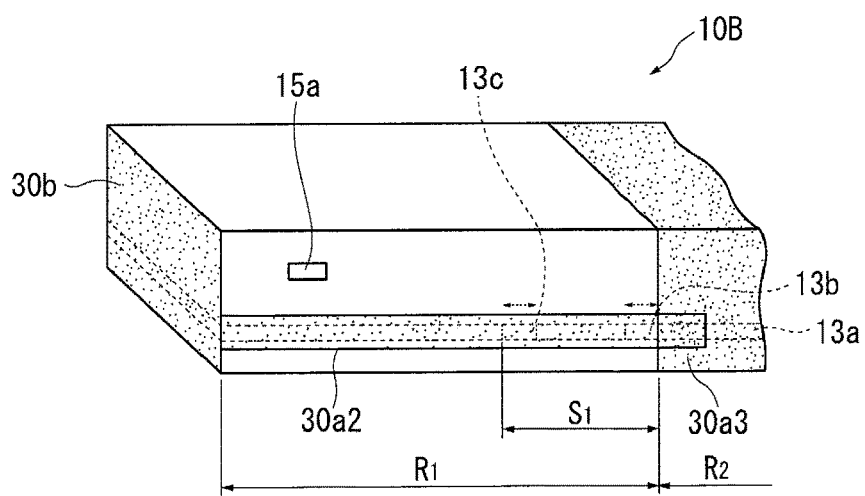
FIG. 5 is a perspective view showing another modification of the glass coatings that cover the NOx sensor element.

As shown in FIG. 5, a rear end portion of the glass coating 30*a*2 may overlap the glass coating 30*a*3. In this case, the formation of a gap between the glass coatings 30*a*2 and 30*a*3 can be prevented, and the third solid electrolyte layer 13*a* of the smallest current cell 13 can be covered in a reliable manner.

Figure 6:
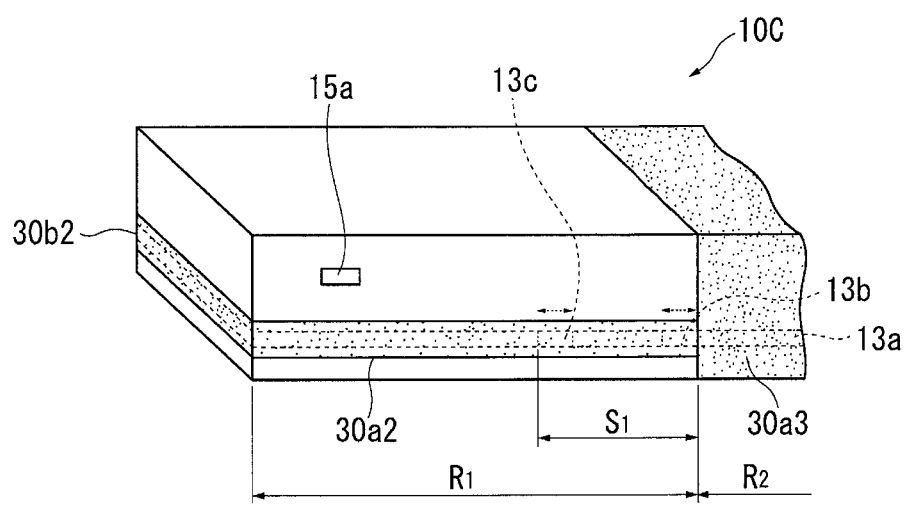
FIG. 6 is a perspective view showing still another modification of the glass coatings that cover the NOx sensor element.

In the NOx sensor elements 10 and 10B in FIGS. 2, 4, and 5, the entire forward-facing surface is covered with the glass coating 30*b*. However, as shown in an NOx sensor element 10C in FIG. 6, only a portion of the forward-facing surface that is located at the same vertical position as the glass coating 30*a*2 in the stacking direction may be coated with a stripe-shaped glass coating 30*b*2.

Example

A glass slurry was applied once by screen printing to side surfaces of an NOx sensor element having the structure described in the above embodiment to a dry thickness of 40 μm (thickness after firing: 20 μm) and then fired at 1,175° C. to produce an Example sample with a glass coating. The glass transition point of the glass coating was 777.7° C. The thicknesses of the glass slurry and the glass coating were measured using a laser film thickness meter, and the glass transition point of the glass coating was measured by DTA (differential thermal analysis).

The glass slurry was obtained by dispersing a glass powder containing silica powder: 60% by mass, alumina: 15% by mass, SrO: 5% by mass, and CaO: 20% by mass by wet mixing. The dispersant used was butyl carbitol.

A comparative sample in which no glass coating was applied to the side surfaces of the NOx sensor element was produced as a Comparative Example.

For each of the Example sample and the comparative sample, the occurrence of Na poisoning was evaluated. In the evaluation, an Na solution was dropped onto a forward end portion of each sample, and then fluctuations in the output from the sensor were checked.

Almost no fluctuations in sensor output were found in the Example sample. However, large fluctuations in sensor output (output current) were found in the comparative sample, and Na poisoning was found to occur.

Next, a glass slurry having the same composition as described above was used to produce a cubic test piece with a mass of 0.25 g under the same firing conditions as described above. The porosity of this test piece was measured by a mercury intrusion method according to JIS-R1655 (2003). Specifically, an automatic porosimeter (AutoPore IV 9500 manufactured by Shimadzu Corporation) was used to measure a pore diameter distribution, and the porosity was automatically computed from the measured pore diameter distribution using software included in the device. The porosity was 2.6%.

DESCRIPTION OF REFERENCE NUMERALS

10 NOx sensor element (gas sensor element)
11 first oxygen pump cell
11*a* first solid electrolyte layer
11*b* the other of first pump electrodes
11*c* one of first pump electrodes
12 oxygen concentration detection cell
12*a* second solid electrolyte layer
12*b* detection electrode
12*c* reference electrode
13 smallest current cell (second oxygen pump cell)
13*a* third solid electrolyte layer
13*b* inner second pump electrode
13*c* counter second pump electrode
16 space (detection chamber)
18 measurement chamber
20 detection element
30*a*, 30*b* glass coating
50 heater
50*a* heat generating element
138 metallic shell (casing)
151 ceramic holder (inner member)
200 gas sensor
O axial line
R1 region including the smallest current cell and extending forward from the smallest current cell

The invention claimed is:

1. A gas sensor comprising:
   a gas sensor element extending in the direction of an axial line and having a forward end portion to be exposed to a target gas;
   a metallic casing that surrounds a circumference of the gas sensor element and has a forward end from which the forward end portion of the gas sensor element protrudes; and
   an insulating inner member contained inside the casing and surrounding the circumference of the gas sensor element,
   wherein the gas sensor element includes:
   a detection element including one or more cells each having a solid electrolyte body and a pair of electrodes, the one or more cells including a smallest current cell in which the smallest current among the cells flows between the pair of electrodes when the gas sensor element is controlled; and a heater stacked on the detection element and including a heat generating element disposed at least in a location that corresponds to the smallest current cell in the direction of the axial line, wherein the solid electrolyte body of the smallest current cell has end faces extending along opposite side surfaces of the detection element and further has an end face extending along a forward-facing surface of the detection element, wherein each of the opposite side surfaces of the detection element has a region including the smallest current cell and extending forward of the smallest current cell in the direction of the axial line, and the region of each of the opposite side surfaces of the detection element and the forward-facing surface of the detection element are covered with a glass coating having a glass transition point of higher than 700° C. but not higher than 800° C. and a porosity of 3.0% or less, and wherein the detection element is controlled at a temperature equal to or lower than the glass transition point of the glass coating.

2. The gas sensor according to claim 1, wherein the glass coating covers portions of the opposite side surfaces of the detection element, the portions extending from the region to a forward end of the inner member in the direction of the axial line.

3. The gas sensor according to claim 1, wherein the detection element further includes a space into which the target gas is introduced, one of the cells is a first oxygen pump cell which includes a first solid electrolyte body and a pair of first pump electrodes disposed on the first solid electrolyte body, one of the first pump electrodes being exposed to the space, the first oxygen pump cell pumping oxygen from/into the target gas in the space, another of the cells is an oxygen concentration detection cell which includes a second solid electrolyte body, a detection electrode disposed on the second solid electrolyte body and exposed to the space, and a reference electrode serving as a counter electrode for the detection electrode, an electromotive force being generated between the reference electrode and the detection electrode, a measurement chamber into which the target gas in the space is introduced, a further one of the cells is a second oxygen pump cell which is the smallest current cell and which includes a third solid electrolyte body, an inner second pump electrode disposed on the third solid electrolyte body and exposed to the measurement chamber, and a counter second pump electrode serving as a counter electrode for the inner second pump electrode, the second oxygen pump cell detecting the concentration of NOx in the target gas in the measurement chamber, the space is formed between the first solid electrolyte body and the second solid electrolyte body stacked that the first solid electrolyte body and the second solid electrolyte body are spaced apart from each other, and the gas sensor element serves as an NOx sensor element.

4. The gas sensor according to claim 2, wherein the detection element further includes a space into which the target gas is introduced, one of the cells is a first oxygen pump cell which includes a first solid electrolyte body and a pair of first pump electrodes disposed on the first solid electrolyte body, one of the first pump electrodes being exposed to the space, the first oxygen pump cell pumping oxygen from/into the target gas in the space, another of the cells is an oxygen concentration detection cell which includes a second solid electrolyte body, a detection electrode disposed on the second solid electrolyte body and exposed to the space, and a reference electrode serving as a counter electrode for the detection electrode, an electromotive force being generated between the reference electrode and the detection electrode, a measurement chamber into which the target gas in the space is introduced, another of the cells is a second oxygen pump cell which is the smallest current cell and which includes a third solid electrolyte body, an inner second pump electrode disposed on the third solid electrolyte body and exposed to the measurement chamber, and a counter second pump electrode serving as a counter electrode for the inner second pump electrode, the second oxygen pump cell detecting the concentration of NOx in the target gas in the measurement chamber, the space is formed between the first solid electrolyte body and the second solid electrolyte body stacked that the first solid electrolyte body and the second solid electrolyte body are spaced apart from each other, and the gas sensor element serves as an NOx sensor element.

* * * * *